United States Patent [19]

Sowers

[11] Patent Number: 5,663,323
[45] Date of Patent: Sep. 2, 1997

[54] SYNTHESIS OF 4-ALKOXY-5-FLUORO-2'-DEOXYURIDINE AND ITS INCORPORATION INTO OLIGONOCLEOTIDES

[75] Inventor: Lawrence C. Sowers, Duarte, Calif.

[73] Assignee: City of Hope, Duarte, Calif.

[21] Appl. No.: 613,582

[22] Filed: Mar. 12, 1996

Related U.S. Application Data

[62] Division of Ser. No. 288,759, Aug. 11, 1994, Pat. No. 5,530,110, which is a continuation of Ser. No. 21,072, Feb. 23, 1993, abandoned.

[51] Int. Cl.$^6$ ............... C07H 1/00; C07H 1/02
[52] U.S. Cl. ............... 536/55.3; 536/25.3
[58] Field of Search ............... 536/55.3, 25.3

[56] References Cited

U.S. PATENT DOCUMENTS 3,404,144  10/1968  Fox et al. ............... 536/28.55
4,754,026   6/1988  Kawada et al. ............... 536/28.55

FOREIGN PATENT DOCUMENTS 0199451  10/1986  European Pat. Off. .

OTHER PUBLICATIONS

Divakar, et al., *J. Chem. Soc. Perkin Trans.*, pp. 1171–1176, 1982.
Chemical Abstracts, vol. 97, No. 7., Abstract No. 56191h, p. 690, 1982, Funai Pharmaceutical Industries, Ltd., Japan Kokai JP 82 28.083.
Martin et al., *J. Pharm. Sci.*, 76(2):1 180–184, 1987.
Sowers et al., *J. Biol. Chem.*, 263(29): 14794–14801 (1988).

*Primary Examiner*—Gary L. Kunz
*Attorney, Agent, or Firm*—Rothwell, Figg, Ernst & Kurz

[57] ABSTRACT

A synthesis of 5-fluoro-2'-ideoxycytidine, of oligonucleotides containing 5-fluoro-2'-deoxycytidine and of certain novel 4-alkoxy-5-fluoro-2'-deoxyuridines is disclosed. These 4-alkoxy compounds are useful intermediates for the preparation of other 4-substituted, 5-fluoro pyrimidine deoxynucleosides, and spontaneously hydrolyze in target cells to form FdU and derivatives thereof.

4 Claims, 4 Drawing Sheets

SYNTHESIS OF 4-ALKOXY-5-FLUORO-2'-DEOXYURIDINE AND ITS INCORPORATION INTO OLIGONOCLEOTIDES

This is a divisional application of U.S. Ser. No. 08/288,759, filed Aug. 11, 1994, now U.S. Pat. No. 5,530,110, which is a continuation of U.S. Ser. No. 08/021,072, filed Feb. 23, 1993, now abandoned.

This invention was made with government support under Grant No. GM 41336 awarded by the National Institutes of Health. The government has certain rights in the invention.

FIELD OF INVENTION

This invention relates to the synthesis of 5-fluoro-2'-deoxycytidine, of oligonucleotides that contain 5-fluoro-2'-deoxycytidine, and of certain novel 4-alkoxy-5-fluoro-2'deoxyuridines. The invention also relates to antitumor agents which comprise such compounds.

BACKGROUND OF THE INVENTION

The 5-fluoropyrimidines comprise an important class of antitumor compounds. One derivative of this class, 5-fluoro-2'-deoxycytidine (FdC) is known to have potent[1-5] and selective[6-8] cytostatic properties. It has been established that FdC can be kinased and deaminated to FdUMP via two distinct metabolic pathways resulting in the inhibition of thymidylate synthase[9]. Due to the increased activity of both cytidine and deoxycytidine deaminases present in many human tumor cells, it has been proposed that FdC might have superior properties as an antitumor agent in man[8].

FdC was first synthesized by Fox et al., via aminolysis of 4-thio,5-fluoro,2'-deoxyuridine[14]. FdC has also been prepared by coupling the fluorinated pyrimidine with a suitably derivatized deoxyribose[15]. Both of these procedures have the disadvantages of modest yield and complexity of products. Robins et al. have presented a method for direct fluorination of deoxycytidine[16]. While FdC was provided in high yield with few side products, the required fluorination reagents are potentially toxic and explosive.

Accordingly, one aspect of the invention comprises a novel method to provide FdC in high yield under mild conditions.

It is also known that FdC has important biochemical properties unrelated to the inhibition of thymidylate synthetase. FdC can induce cellular differentation[10] and cause dramatic decreases in DNA 5-methylcytosine levels[10,11]. FdC is incorporated into cellular DNA and it has been shown that the level of FdC incorporation is proportional to cytotoxicity[11]. Recently, interest in FdC has been renewed as it has been shown that oligonucleotides containing FdC are potent mechanism based inhibitors of both procaryotic[12] and eucaryotic[13] DNA (cytosine-5) methyltransferases.

Physical and biochemical studies aimed at elucidation of the mechanisms which explain the biological properties of FdC require methods for synthesis of FdC in oligonucleotides at unique sites. Previously, FdC has been introduced into oligonucleotides by incorporation of FdCTP by DNA polymerase[4,5]. This method suffers from the disadvantage that FdC would be incorporated at multiple sites and quantities sufficient for physical studies are not practically attainable. It has been reported that attempts to prepare FdC containing oligonucleotides via standard methods for deoxycytidine incorporation fail because the N-benzylated derivative of FdC decomposes under normal synthetic conditions[4].

Accordingly, another aspect of this invention provides a practical method for preparing oligonucleotides containing FdC.

SUMMARY OF THE INVENTION

Pursuant to one aspect of the invention FdC is generated via the intermediate 4-alkoxy-5-fluoro-2'-deoxyuridine (4-alkoxy FdU). The intermediate 4-alkoxy nucleosides demonstrate cytotoxic activity and significantly enhanced lypophility and hydrolyze to FdU.

Pursuant to another aspect of the invention, FdC is generated in oligonucleotides by aminolysis of oligonucleotides containing 4-alkoxy-5-fluoro-2'-deoxyuridine moieties. See FIG. 2.

The invention also includes a class of novel compounds having the structural formula

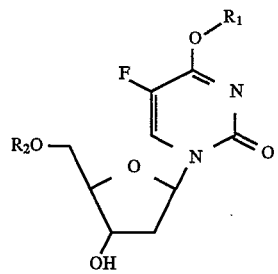

in which $R_1$ is a straight or branched chain alkyl group having from one to eighteen carbons, where $R_2$ is hydrogen, a phosphate thiophosphate, phosphate ester or thiophospate ester. Thus $R_1$ may be ethyl, propyl, isopropyl, butyl, isotutyl, hexyl or any two to eighteen carbon atom straight or branched chain alkyl group. The $R_1$ group may include double or triple carbon to carbon atom bonds. The $R_1$ group may also be substituted by chlorine, bromine, fluorine or iodine, by a primary, secondary or tertiary amino group, by $—NO_2$ or by other substituents. These compounds spontaneously hydrolyze in target cells to form the active chemotherapy agent FdU and derivatives thereof.

DETAILED DESCRIPTION OF THE INVENTION

Synthesis of FdC

The synthetic route employed by the invention for the conversion of FdU to FdC is similar to that presented previously by Divakar and Reeses for the conversion of araU to araC[17] except for the introduction of the intermediate 4-alkoxy derivatives described here. Due to the greater reactivity of the 5-fluoro derivatives, certain modifications are employed to achieve the conversion of FdU to FdC in high yield under mild conditions.

Figure 1:
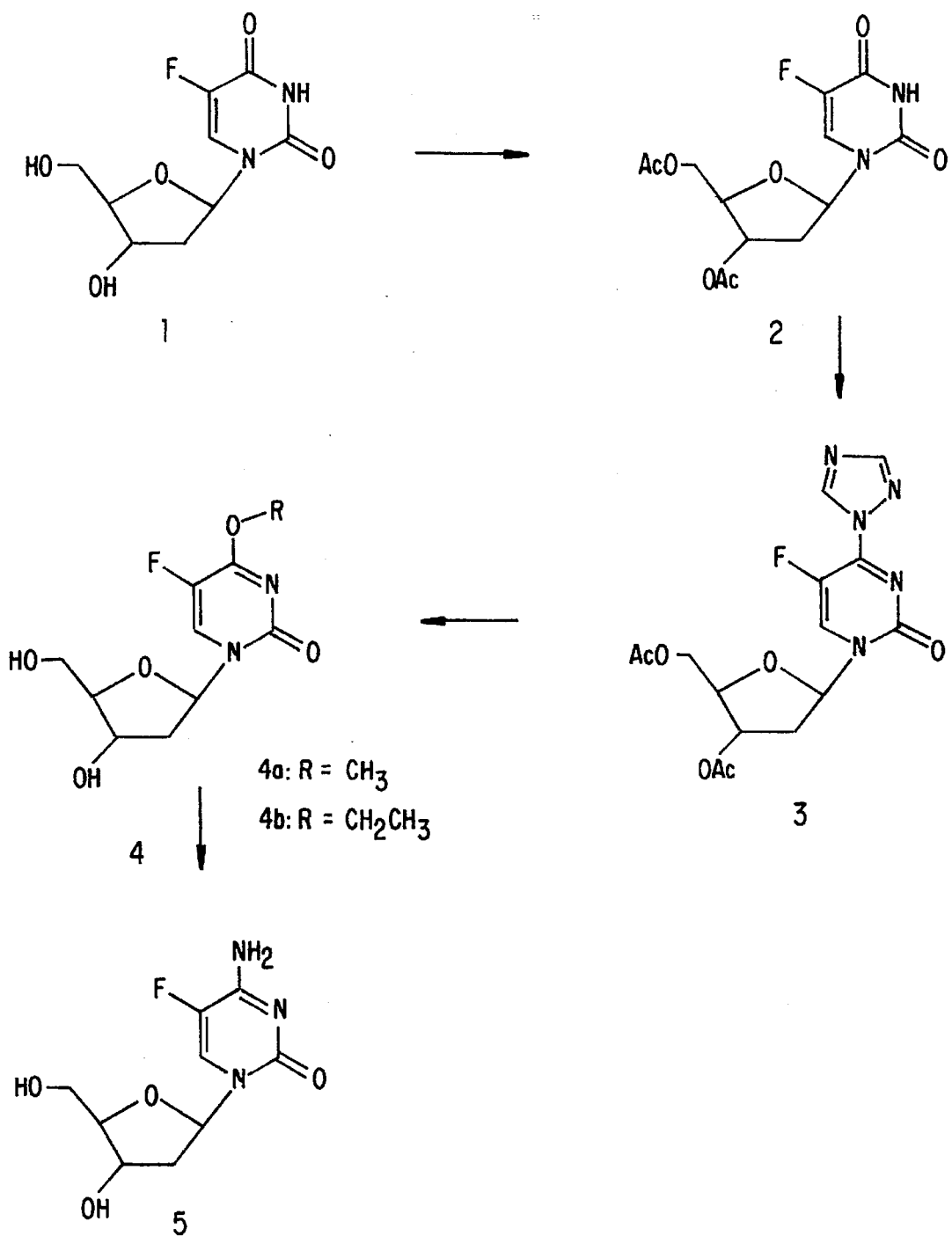
FIG. 1 depicts a reaction scheme for the production of FdC by one embodiment of the invention. Note that the Figure ascribes numbers 1 to 3, 4a, 4b and 5 to the various compounds which are repeated in the text in the detailed description of the invention.

As exemplified by FIG. 1, the sugar hydroxyls of FdU (1) acetylated with acetic anhydride in pyridine. This reaction proceeded in near quantitative yield. Solvent and excess acetylating agent were removed under reduced pressure and the resulting white diacetyl derivative (2) was converted in the same flask to the 4-triazole intermediate (3). The progress of the reaction was followed by changes in the ultraviolet spectrum of an aliquot in methanol. The absorbance maxima of the starting material is 271 nm whereas that of the triazole intermediate is 331 mn.

In the Divakar and Reese procedure[17] the 4-triazole intermediate was washed with bicarbonate solution. However, it was applicant's experience that this resulted in significant decomposition of the triazole intermediate (3), even with freshly prepared bicarbonate. Attempts to isolate the intermediate triazole derivative by either crystallization or silica gel column chromatograph invariably resulted in the generation of large amounts of compound (2). Attempts to convert the crude triazole derivative into FdC with either ammonium hydroxide or ethanolic ammonia, resulted in the recovery of significant amounts of FdU.

Pursuant to the invention the triazole intermediate (3) was converted into the alkoxy derivatives with either sodium methoxide (4a) or ethoxide (4b). Displacement of the triazole group with alkoxy proceeded in high yield with simultaneous deprotection of the sugar moiety. The 4-alkoxy deoxynucleosides (4) are easily separated by silica gel chromatography. Yields for the ethoxy proved superior to methoxy derivative yields.

The alkoxy derivatives were converted to FdC (5) with ethanolic ammonia. The 4-ethoxy-5-fluoro-2'-deoxyuridine (4b) is converted to FdC quantitatively with ethanolic ammonia overnight at room temperature, whereas treatment of the methoxy derivative (4a) with methanolic ammonia generates significant amounts of FdU (1). The FdC formed from the ethoxy derivative is analytically pure and does not require subsequent chromatography. FdU may therefore be converted to FdC via the 4-ethoxy derivative in 78% yield.

In aqueous solution, the 4-alkoxy derivatives (4) are converted to FdU (1). The reaction is followed by changes in the UV spectrum which demonstrate an isosbestic point at 276 mn. The reaction is both acid and base catalyzed. At pH 11, the half lives for the conversion are 3.3 and 12.5 hours, respectively for the methoxy (4a) and ethoxy (4b) derivatives. The rate of hydrolysis was found to be directly proportional to the hydroxide concentration.

At pH 8, the alkoxy derivatives are electronically neutral and are significantly more lipophilic than the parent compound, FdU. The relative partition coefficients between 0.1M phosphate buffer, pH 7.0 and 1-octanol[18] were determined to be FdU (1), 0.053; FdC (5), 0.028; 4-methoxyFdU (4a), 0.24; 4-ethoxyFdU (4b), 0.78.

Biological Testing

Cell culture and cytostatic activity (growth inhibition): The human T-cell line CCRF-CEM was obtained from J. S. Holcenberg, Childrens Hospital of Los Angeles. Maintenance of cultures in RPMI 1640 medium and growth inhibition assays were carried out as previously described[24] except that iron-supplemented bovine calf serum was used routinely in place of dialyzed fetal bovine serum and inhibition of cell growth was based on the culture densities after four days without dilution of the cultures. Triplicate culture wells were counted for each drug concentration and the mean values were used to calculate the $EC_{50}$S by linear interpolation between the concentrations of each drug which yielded culture densities immediately above and below 50% of the density of the drug-free control cultures. Culture densities were also determined after three days to check that the cell growth continued in cultures without cytotoxic agents.

As shown in Table 1, the four 5-fluoropyrimidines FdU, FdC, 4a and 4b demonstrate cytotoxicity toward CCRF-CEM cells in culture:

TABLE 1

| compound | $EC_{50}$ |
|---|---|
| FdUrd (1) | 8.9 nM |
| FdCyd (5) | 6.9 nM |
| 4-methoxy-FdUrd (4a) | 1.8 μM |
| 4-ethoxy-FdUrd (4b) | 1.8 μM |
| fluorouracil | 5.0 μM |

As Table 1 shows, the relative order of activity is FdC (5)>FdU (1)>4-ethoxyFdU (4b)>4-methoxyFdU (4a). The greater toxicity of FdC is likely the result of multiple mechanisms of action.

The alkoxy derivatives have activity similar to 5-fluorouracil which is in regular clinical use. The major limitation to the in vivo activity of FdUrd is cleavage via plasma thymidine phosphorylase, and neither deoxycytidine derivatives[25] nor 4-methoxy-5-fluoro-2'-deoxyuridine[26] are catabolized via this pathway. Unlike both fluorouracil and FdUrd, the alkoxy derivatives are electronically neutral at physiological pH. The alkoxy derivatives are significantly more lipophilic, and the lipophilicity is related the the length of the 4-alkoxy group.

Previously, it has been shown that the nucleoside analogue AZT can enter human erythrocytes and lymphocytes by nonfacilitated diffusion[18]. This unusual property was explained based upon the increased lipophilicity (20 fold) of AZT over dT. The alkoxy derivatives (4a) and (4b) are more lipophilic than FdU (4.5 and 14.7 fold, respectively). The 4-alkoxy derivatives and the related compounds encompassed by Formula I may therefore enter cells via both facilitated transport because the 3'hydroxyl is still intact and by nonfacilitated diffusion due to enhanced lipophilicity.

EXAMPLE I

This Example describes the actual procedures depicted by FIG. 1.

Materials and Chemical Procedures

FdU was obtained from QUAD Pharmaceutical, Inc. All other chemicals were obtained from Aldrich Chemical Co. Pyridine and acetonitrile were distilled and stored over molecular sieves. All other chemicals were used without further purification. Proton NMR spectra were recorded at 500 MHz on a Bruker AMX500. Mass spectra were obtained with a JEOL FX-100 using a glycerol matrix. The instrument was operated in the positive ion mode and samples were chemically ionized (CI). UV spectra were obtained with a Cary 219 UV/visible spectrophotometer. Thin layer chromatography was performed with silica gel plates developed with 10% methanol in dichloromethane. Column chromatography utilized 60–120 mesh silica gel and methanol in dichloromethane. The pH of aqueous solutions was determined with a Fisher Accumet pH meter.

Biological Testing

CCRF-CEM cells were a gift from Dr. John Holcenberg and were grown in suspension as previously described.

Chemistry

3',5'-diacetyl-5-fluoro-2'-deoxycytidine (2)

FdU (2g, 8.1mmol) was dried twice by evaporation of pyridine and was resuspended in 50 ml dry pyridine. Five equivalents of acetic anhydride (3.82 ml) were added dropwise. The progress of the reaction was assayed by TLC. After two hours, an excess of methanol was added and the reaction stirred for ten minutes. Solvent was removed under reduced pressure to yield a clear glass which was dried to a white powder by coevaporation of toluene. The yield of (2) was 2.65 g (quantitative conversion) which was analytically pure. TLC R 0.85 in 10% MeOH/CH$_2$Cl$_2$, $^1$H NMR (D$_6$DMSO) ppm 11.90 (1H, s, NH), 7.97 (1H, d, CH$_6$), 6.14 (1H, t, H1'), 5.17 (1H, m, H3'), 4.24 (2H, d, H5'), 4.16 (1H, m, H4'), 2.47 (1H, m, H2'/H2"), 2.29 (1H, m, H2'/H2") 2.06 (6H, s, acetyl). M+H/e calcd 331.0941, found 331.1010. Anal. (C$_{13}$H$_{15}$N$_2$O$_7$F) C,H,N,F.

3',5'-diacetyl-4-triazole-5-fluoro-2'-deoxyuridine (3)

To 50 ml dry acetonitrile in an ice bath was added 1,2,4-triazole (5.04 g, 9 eq) and phosphoryl chloride (1.51 ml, 2 eq). Triethylamine (9.7 ml, 8.6 eq) was then added dropwise. DiacetylFdU (2) in 50 ml dry acetonitrile (8.1 mmol) was then added dropwise to the solution containing the triazole reagent over a period of five minutes. The progress of the reaction was monitored by changes in the UV spectra of an aliquot of the reaction mixture in MeOH. After 45 minutes at ice bath temperature, the reaction was quenched by the addition of triethylamine (6.76 ml, 6 eq) and water (1.75 ml, 12 eq). Solvent was evaporated under reduced pressure. The identity of the intermediate was confirmed by mass, NMR and UV spectroscopy. The 4-triazole intermediate is a highly reactive compound and attempts to obtain an analytically pure sample for elemental analysis either by chromatography or recrystallization invariably resulted in the generation of significant amounts of the 4-keto starting material (2). TLC R$_f$ 0.90 in 10% MeOH/CH$_2$Cl$_2$, $^1$H NMR ppm 9.37 (1H, s, imidazole), 8.64 (1H, d, H$_6$), 8.43 (1H, s, imidazole), 6.15 (1H, t, H1'), 5.18 (1H, m, h3'), 4.27 (2H, d, H5'), 4.19 (1H, m, H4') 2.47 (1H, m, H2'/H2"), 2.25 (1H, m, H2'/H2"), 2.09 (6H, s, acetyl). TLC R$_f$ 0.90 (10% MeOH/CH$_2$Cl$_2$). UV (MeOH) 331 (3,290), 293 (1,270), 254 (5,850), 232 (2,810) M+H/e calcd (C$_{15}$H$_{17}$N$_5$O$_6$F) 382.1162, found 382.1106.

4-Methoxy-5-fluoro-2'-deoxyuridine (4a)

Half of the crude triazole reaction mixture (3) was dried by evaporation of solvent under reduced pressure and then twice from MeOH. The residue was then suspended in 50 ml MeOH and a solution of 3.5 eq NaOMe in 50 ml MeOH was added. TLC revealed complete conversion in less than ten minutes. Solvent was evaporated and compound 4a was isolated by silica gel chromatography. Obtained 0.78 g, 74% yield from FdU. TLC R$_f$ 0.29 (10% MeOH/CH$_2$Cl$_1$). 1H NMR 8.47 (1H, d H6), 6.06 (1H, t, H1'), 5.31 (1H, d, 3'OH) 5 23 (1H, t, 5'OH), 4.22 (1H, q, H3'), 3.91 (3H, s, O—CH$_3$), 3.82 (1H, q, H4') 3.59 (2H, m, h5'/H5"), 2.22 (1H, m, H2'/H2"), 2.05 (1H, m, H2'/H2"). UV (pH 7.0) 284nm (6,324), 242nm (766). M+H/e calcd 261.0886, found 261.0933. Anal (C$_{10}$H$_{13}$N$_2$O$_5$F) C,H,N,F.

4-Ethoxy-5-fluoro-2'-deoxyuridine (4b)

The 4-ethoxy compound (4b) was prepared as above with sodium ethoxide in ethanol. Displacement of the triazole moiety was very rapid, however, deprotection of the sugar required stirring at room temperature for 30 minutes. Solvent was removed under reduced pressure and the compound isolated by silica gel column chromatograph. Obtained 0.89 g, 80% yield from FdU. TLC R$_f$ 0.31 (10% MeOH/CH$_2$Cl$_2$). $^1$H NMR ppm 8.47 (1H, d, H6), 6.06 (1H, t, H1'), 5.24 (1H, d, 3'OH), 5.18 (1H, t, 5'OH), 4.37 (2H, m, O—CH$_2$—CH$_3$), 4.23 (1H, m, H3'), 3.83 (1H, m, H4'), 3.67 (2H, m, H5'/H5") 2.24 (1H, m, H2'/H2") 2.05 (1H, m, H2'/H2"), 1.32 (3H, m, O—CH$_2$CH$_3$). UV (pH 7.0) 284nm (6,324) 242 nm (811). M+H/e calcd 275.1043, found 275.0976. Anal. (C$_{11}$H$_{15}$N$_2$O$_5$F) C,H,N,F.

5-Fluoro-2'-deoxycytidine (5)

The 4-ethoxy derivative (4b) (0.5 g, 1.8 mmol) was treated with ethanolic ammonia at room temperature overnight. Solvent was removed under reduced pressure. TLC revealed complete conversion to 5-fluoro-2'-deoxycytidine. Obtained 0.44 g, 98% purified-yield from compound 4b, 78% overall yield. TLC R$_f$ 0.11 (10% MeOH/CH$_2$Cl$_2$). $^1$H NMR ppm 8.08 (1H, d, H6), 7.73 (1H, broad singlet, amino) 7.49 (1H, broad singlet, amino) 6.09 (1H, t, h1') 5.22 (1H d, 3'OH) 5.11 (1H, t, 5'OH) 4.21 (1H m, H3'), 3.76 (1H, m, H4'), 3.56 (2H, m, H5'/H5"), 2.11 (1H, m, H2'/H2"), 1.97 (1H, H2'/H2"). UV (pH 7.0) 280 (8,700) 258 (5,890). M+H/e calcd 246.0890, found 246.0897. Anal. (C$_9$H$_{12}$N$_3$O$_4$F) C,H,N,F.

Hydrolysis of the alkoxy derivatives (4a and 4b)

Solutions of 4-methoxy (4a) and 4-ethoxy-5-fluoro-2'-deoxyuridine (4b) (1.5×10$^{-4}$M) were prepared in unbuffered, deionized water. The pH of the solutions was adjusted with the addition of 1N NaOH or 1N HCl. Both alkoxy derivatives were converted quantitatively to FdU in aqueous solution. An isosbestic point was observed in the UV spectrum of the solutions at 276 nm. The UV spectrum obtained upon completion of the hydrolysis in both with both compounds 4a and 4b are indistinguishable from FdU[9]. At pH 11, the conversion half lives (4→1) were found to be 2.2H and 12.5H at 25° for the methoxy and ethoxy derivatives, respectively. It was found that the observed hydrolysis rate for both compounds was proportional to [$^-$OH] (data not shown).

Incorporation of Fdc into Oligonucleotides

Figure 2:
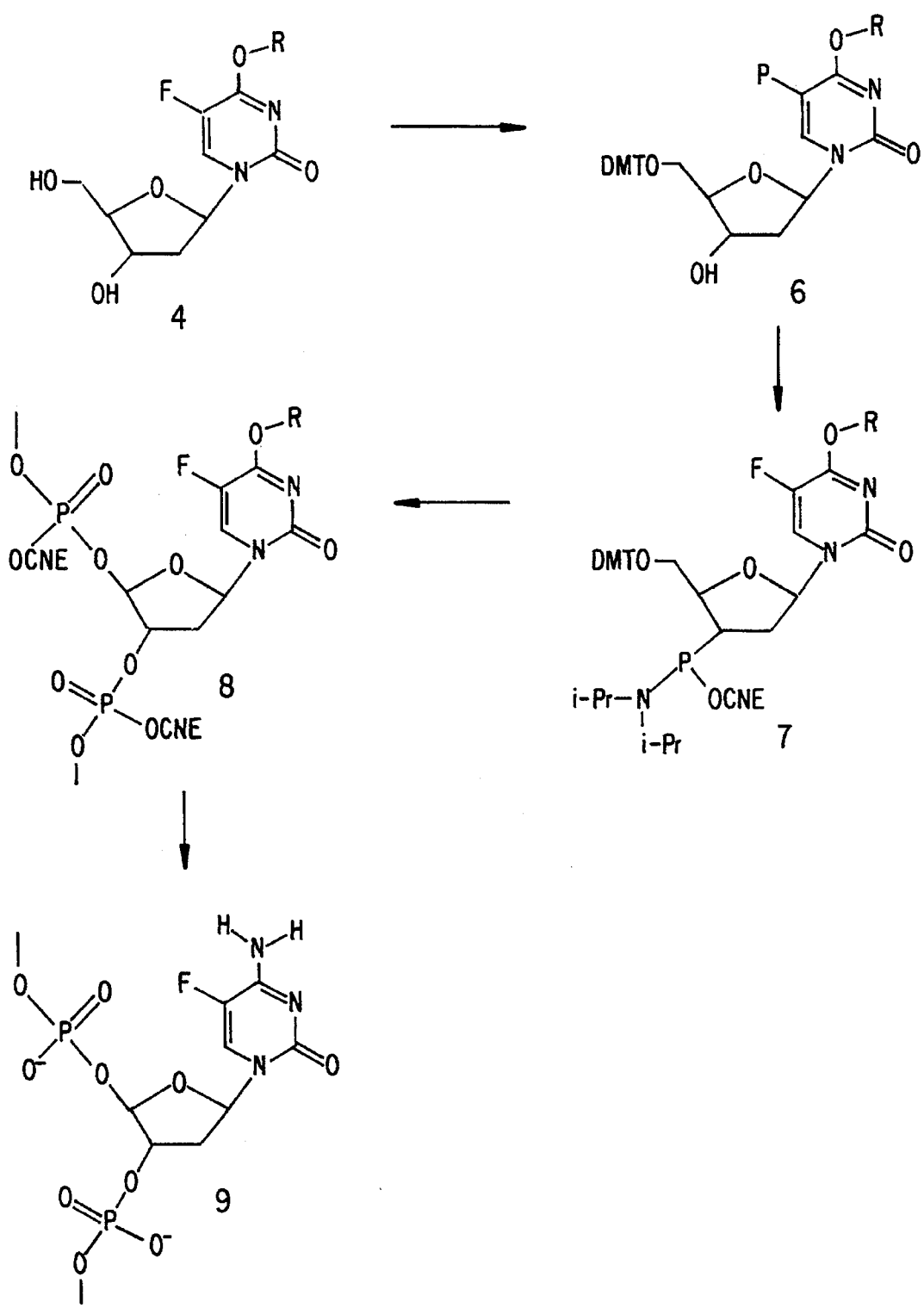
FIG. 2 depicts a reaction scheme for the synthesis of oligonucleotides containing FdC by another embodiment of the invention. Note that the Figure ascribes numbers 4b, 6, 7, 8, and 9 to the various compounds involved. These designations are repeated in text in the detailed description of the invention.

The incorporation of FdC into an oligonucleotide by the method of this invention is illustrated by FIG. 2. Compound 4b was used as a precursor for the synthesis. The 4b compound was converted to the 5'-O-dimethoxytrityl-3'-O-(N,N-diisopropylcyanoethyl) phosphoramidite (4b→6→7) by standard procedures.[19-21] Compound (6) $^1$H NMR (DMSO d$_6$) 7.9 (d,1,H5), 7.3 (9,m,Ar), 6.9 (4,m,Ar), 6.2 (t,1,H1'), 5.4 (d,1,3'OH), 4.3 (m,3,O—CH$_2$CH$_3$), 3.9 (m,1, H4'), 3.4 (m,2,H5'), 2.87 (s,3,OCH$_3$), 2.85 (s,3,OCH$_3$), 2.2 (2,m,H2'), 1.15 (t,3 OCH$_2$CH$_3$). Compound (7) $^{31}$P NMR (Cl$_3$CD) 146.9, 146.4.) A seven base oligodeoxynucleotide 3'd(C G G FC G A C) was synthesized manually at the 20 µmole scale using standard phosphoramidite methods. The O$^4$EtFdU amidite (6) coupled to the oligonucleotide with an efficiency indistinguishable from the coupling of the normal amidites (>98%).

After synthesis, the oligonucleotide was deprotected in ethanolic ammonia at 60° C. for 12 hours (9→10). The oligonucleotide containing a 5trityl group was purified by reverse phase HPLC. Following detritylation with 80% acetic acid, the oligonucleotide was again purified by ion exchange HPLC. Excess salt was removed by dialysis.

A portion of the purified oligonucleotide was enzymatically digested with nuclease P1 and bacterial alkaline phosphatase.[22] The deoxynucleosides generated by digestion were analyzed by reverse phase HPLC. (Note: HPLC utilized a Perkin Elmer series 4 gradient pump and a Pharmacia/LKB spectral diode array detector. Separation of deoxynucleosides was achieved with a Supleco LC-18S column eluted with 0.05M sodium phosphate, pH 4.5, and an increasing linear methanol gradient (3–50%).) The deoxynucleosides dC, FdC, dG and dA were present in the correct ratios based upon integration of the chromatogram peaks. The identity of the FdC peak was confirmed by cochromatography with authentic FdC and by the characteristic UV spectra of the chromatogram peak measured with a photodiode array detector.

Notably absent from the chromatogram was a peak which would correspond to FdU. Previously attempted FdC oligo synthesis using 4-methoxy FdU followed by deprotection with methanolic ammonia resulted in significant hydrolysis with formation of FdU.

Figure 3:
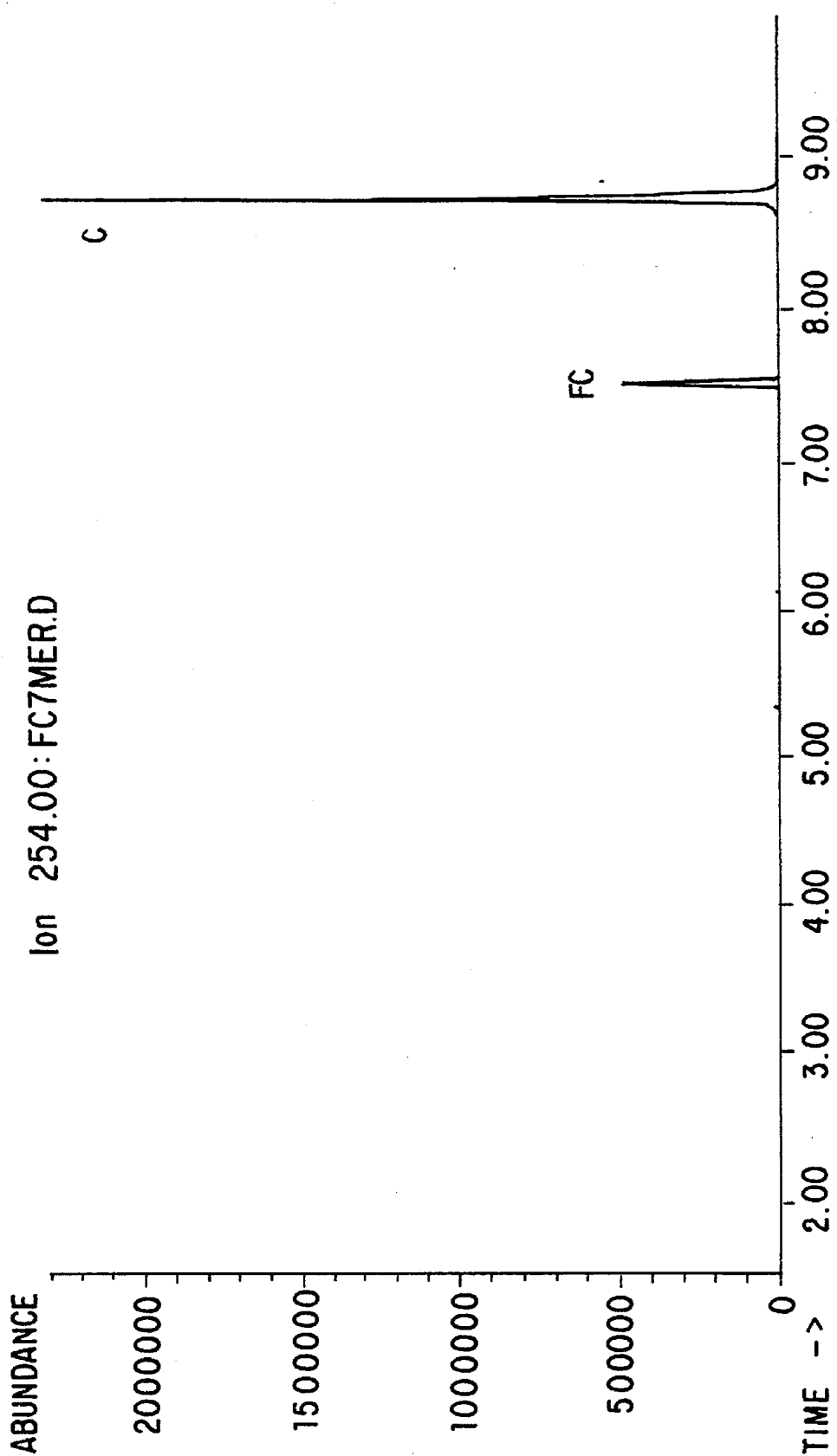
FIG. 3 depicts a gas chromatogram of hydrolyzed cytosine (C) and fluorocytosine (FC) from a seven base oligonucleotide containing FdC.
Figure 4:
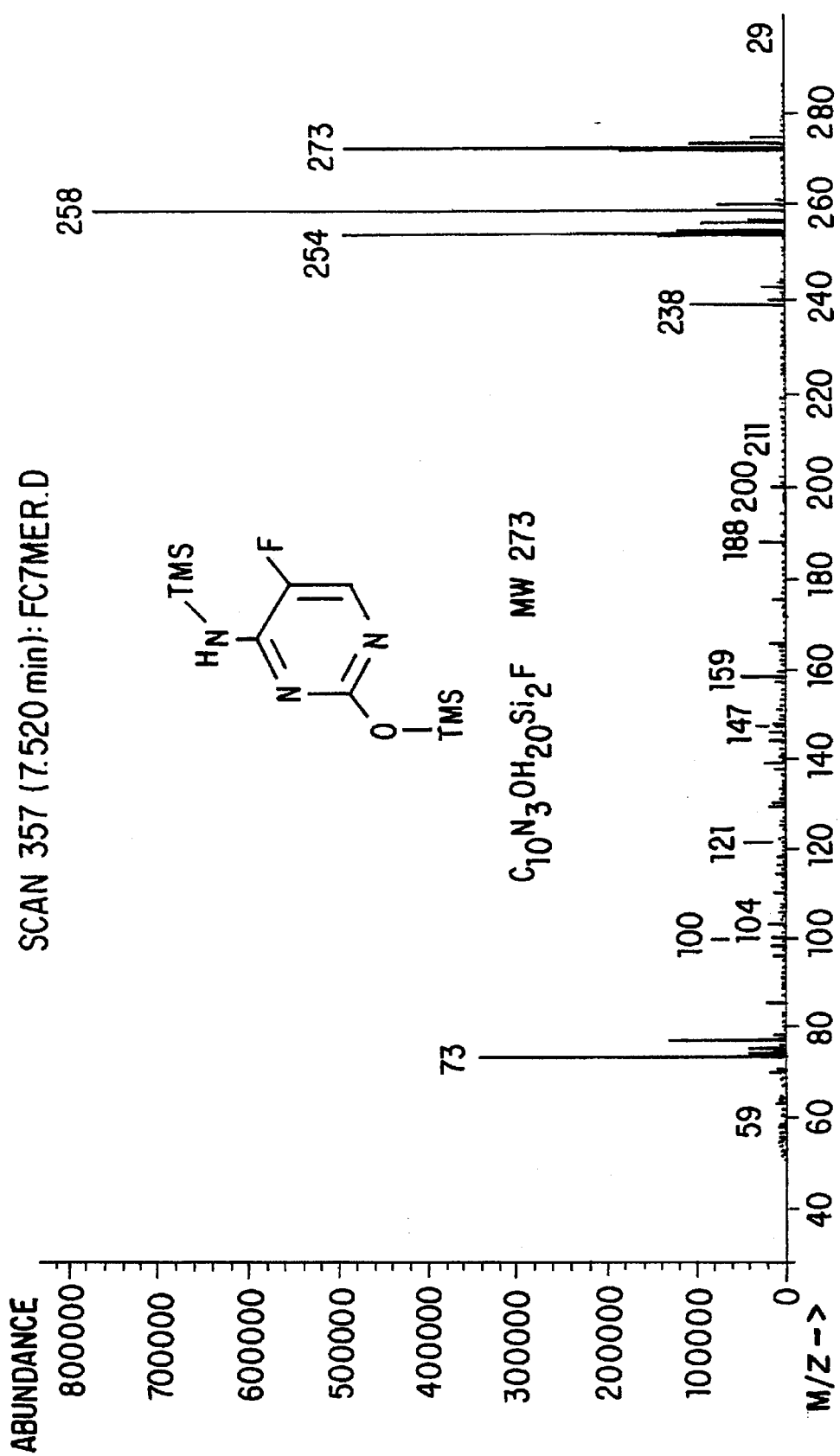
FIG. 4 is a mass spectrum of the silylated FC peak shown in FIG. 3.

To further confirm its composition, the FdC oligonucleotide was acid hydrolyzed in formic acid. The liberated bases were silylated (TMS) and then analyzed by GCMS. The method of Dizdaroglu[23] was used for the preparation of bases for GCMS analysis and for GCMS conditions. Instrumentation consisted of an HP5070B mass selective detector with a modified Phrasor Scientific high energy dynode and an HP 5890A gas chromatograph. The selected ion chromatogram at 254 amu is shown by FIG. 3. Cytosine and 5-substituted cytosine derivatives have a characteristic fragment ion at 254 amu. The mass spectrum of the silylated fluorocytosine peak is shown by FIG. 4. The parent ion is observed at 273 amu. The most abundant ion is observed at 258 amu corresponding to a loss of a methyl group from the trimethylsilyl derivative. The 254 amu ion results from loss of fluorine.

BIBLIOGRAPHY

1. Eidinoff, M. L, et al., *Cancer Res.* 19:638–642 (1959).
2. Burchenal, J., et al., *Cancer Res.* 19:495–500 (1959).
3. Cheong, et al, *Cancer Res.* 20:1602–1607 (1960).
4. Mukherjee, K., et al., *Cancer Res.* 22:815–822 (1962).
5. Khwaja, T. A., et al. *J.Med. Chem.* 13:64–69 (1970).
6. Mekras, J., et al. *Cancer Res.* 44:2552–2560 (1984).
7. Boothman, et al., *Mol. Pharmacol.* 27:584–594 (1985).
8. Boothman, et al., *Pharmac. Ther.* 42:65–88 (1989).
9. Newman, et al., *Proc. Natl. Acad. Sci. USA* 79:6419–6423 (1982).
10. Jones, P. A., et al., *Cell* 20:85–93 (1980).
11. Kaysen, J., et al., *Cancer Res.* 46:4534–4538 (1986).
12. Osterman, D. G., et al, *Biochemistry* 27:5204–5210 (1988).
13. Smith, S. S., et al., *Proc. Natl. Acad. Sci. USA* (in press).
14. Wempen, I., et al., [*Cite*] 83, 4775 (1961).
15. Hoffer, M., et al., *J.Am. Chem. Soc.* 81:4112 (1959).
16. Robins, M. J., et al., *Am. Chem. Soc.* 98:7381 (1976).
17. Divakar, K. J., et al., *J.C.S. Perkin I* 1982, 1171 (1982).
18. Zimmerman, E. P., et al., *J. Biol. Chem.* 262:5748–5754 (1987).
19. Sowers, L. C., et al., *J. Biol. Chem.* 263:14794–14801 (1988).
20. Li, B. F. L., et al., *Biochemistry* 26:1086–1093 (1987).
21. Gait, M. J., Oligonucleotide Synthesis: *A Practical Approach*, IRL Press, Washington (1985).
22. Palmgren, G., et al., *Biochim.Biophys.Acta* 1049:293–297 (1990).
Dizdaroglu, M., *J.Chromatography* 295:103–121 (1984).
24. Keyomarsi, K., et al., *Cancer Res.* 46:5229–5235 (1986).
25. de Verdier, C. -H., et al., *J Natl. Cancer Inst.* 24:13–29 (1960).
26. Kent, R. J., et al., *J. Med. Chem.* 13:70–73 (1970).

I claim:

1. A method for synthesizing 5-fluoro, 2'-deoxycytidine which comprises:

(a) reacting a triazole having the structural formula I

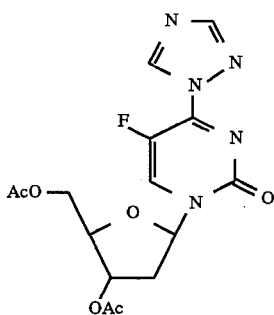

with an alkali metal alkoxide having the formula

in which X is an alkali metal and R is a straight or branched chain alkyl group having from one to eighteen carbon atoms to produce a compound having the formula II

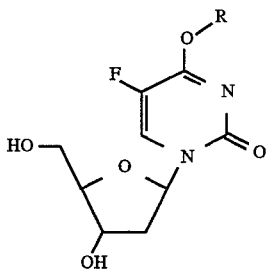

and (b) reacting said compound having the formula II with a nucleophile base to produce 5-fluoro-2'-deoxycytidine.

2. A method as defined by claim 1 in which alkali metal alkoxide utilized in step (a) is sodium methoxide or sodium ethoxide and in which the base utilized in step (b) is ethanolic ammonia.

3. In a process for preparing 5'-O-dimethoxytrityl-3'-O—(N,N-diisopropylcyanoethyl)nucleoside phosphoramidite and then incorporating said phosphoramidite into an oligonucleotide, wherein the improvement is use of the nucleoside shown below as the precursor of the phosphoramidite:

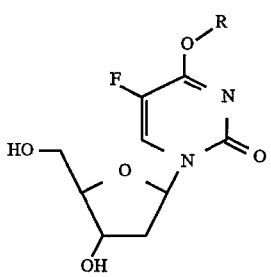

wherein R is an alkyl group having from 1 to 18 carbon atoms.

4. A method as defined by claim 3, in which R is ethyl.

* * * * *